United States Patent
Hikosaka

(10) Patent No.: US 11,464,476 B2
(45) Date of Patent: Oct. 11, 2022

(54) RADIATION IMAGING SYSTEM, CONTROL APPARATUS, CONTROL METHOD, AND COMPUTER READABLE MEDIUM

(71) Applicant: CANON KABUSHIKI KAISHA, Tokyo (JP)

(72) Inventor: Manami Hikosaka, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 161 days.

(21) Appl. No.: 16/694,790

(22) Filed: Nov. 25, 2019

(65) Prior Publication Data

US 2020/0170609 A1 Jun. 4, 2020

(30) Foreign Application Priority Data

Nov. 29, 2018 (JP) .............................. JP2018-224270

(51) Int. Cl.
G06F 11/07 (2006.01)
A61B 6/00 (2006.01)
G06F 11/14 (2006.01)

(52) U.S. Cl.
CPC ............ *A61B 6/586* (2013.01); *A61B 6/4494* (2013.01); *A61B 6/54* (2013.01); *A61B 6/545* (2013.01); *A61B 6/58* (2013.01); *G06F 11/0727* (2013.01); *G06F 11/1448* (2013.01); *G06F 11/1456* (2013.01); *G06F 11/1461* (2013.01); *G06F 11/1469* (2013.01); *A61B 2560/0276* (2013.01)

(58) Field of Classification Search
CPC ............. G06F 11/0727; G06F 11/1448; G06F 11/1469
See application file for complete search history.

(56) References Cited

U.S. PATENT DOCUMENTS

| | | | | |
|---|---|---|---|---|
| 5,077,768 A * | 12/1991 | Shigyo | .................. | G01T 1/2012 378/98 |
| 2003/0069503 A1* | 4/2003 | Matsui | .................. | A61B 8/465 600/437 |
| 2009/0083072 A1* | 3/2009 | Osawa | .................. | G16H 50/20 705/2 |
| 2011/0135214 A1* | 6/2011 | Tanabe | .................. | G06T 5/003 382/254 |
| 2013/0102245 A1* | 4/2013 | Ohguri | .................. | A61B 6/548 455/39 |
| 2013/0184537 A1* | 7/2013 | Konuma | ................ | A61B 6/586 600/300 |

(Continued)

FOREIGN PATENT DOCUMENTS

JP 2001-161648 A 6/2001
JP 2011-36560 A 2/2011

(Continued)

*Primary Examiner* — Kamini B Patel
(74) *Attorney, Agent, or Firm* — Canon U.S.A., Inc. IP Divison

(57) ABSTRACT

A radiation imaging system includes a setting information storage that stores setting information to be used for radiation imaging, a setting information backup unit configured to back up the setting information stored in the setting information storage, and an operation control unit configured to restore, in a case the setting information storage has failed, the setting information in the setting information storage based on the setting information backed up in the setting information backup unit.

30 Claims, 8 Drawing Sheets

(56) References Cited

U.S. PATENT DOCUMENTS

| | | | |
|---|---|---|---|
| 2013/0243300 A1* | 9/2013 | Oda | A61B 6/542 |
| | | | 382/132 |
| 2015/0199813 A1* | 7/2015 | Yamahana | A61B 6/5258 |
| | | | 378/8 |
| 2016/0094700 A1* | 3/2016 | Lee | H04W 8/245 |
| | | | 455/419 |
| 2016/0124619 A1* | 5/2016 | McCallum | G16H 10/20 |
| | | | 345/619 |
| 2017/0143996 A1* | 5/2017 | Prosser | A61N 5/1045 |
| 2017/0231596 A1* | 8/2017 | Fieselmann | A61B 6/0407 |
| | | | 378/207 |
| 2018/0144823 A1* | 5/2018 | Raman | A61B 5/055 |
| 2018/0271474 A1* | 9/2018 | Nishijima | A61B 6/586 |
| 2019/0231299 A1* | 8/2019 | Lalena | A61B 6/5205 |

FOREIGN PATENT DOCUMENTS

| | | |
|---|---|---|
| JP | 2011-128819 A | 6/2011 |
| JP | 2017-189240 A | 10/2017 |

\* cited by examiner

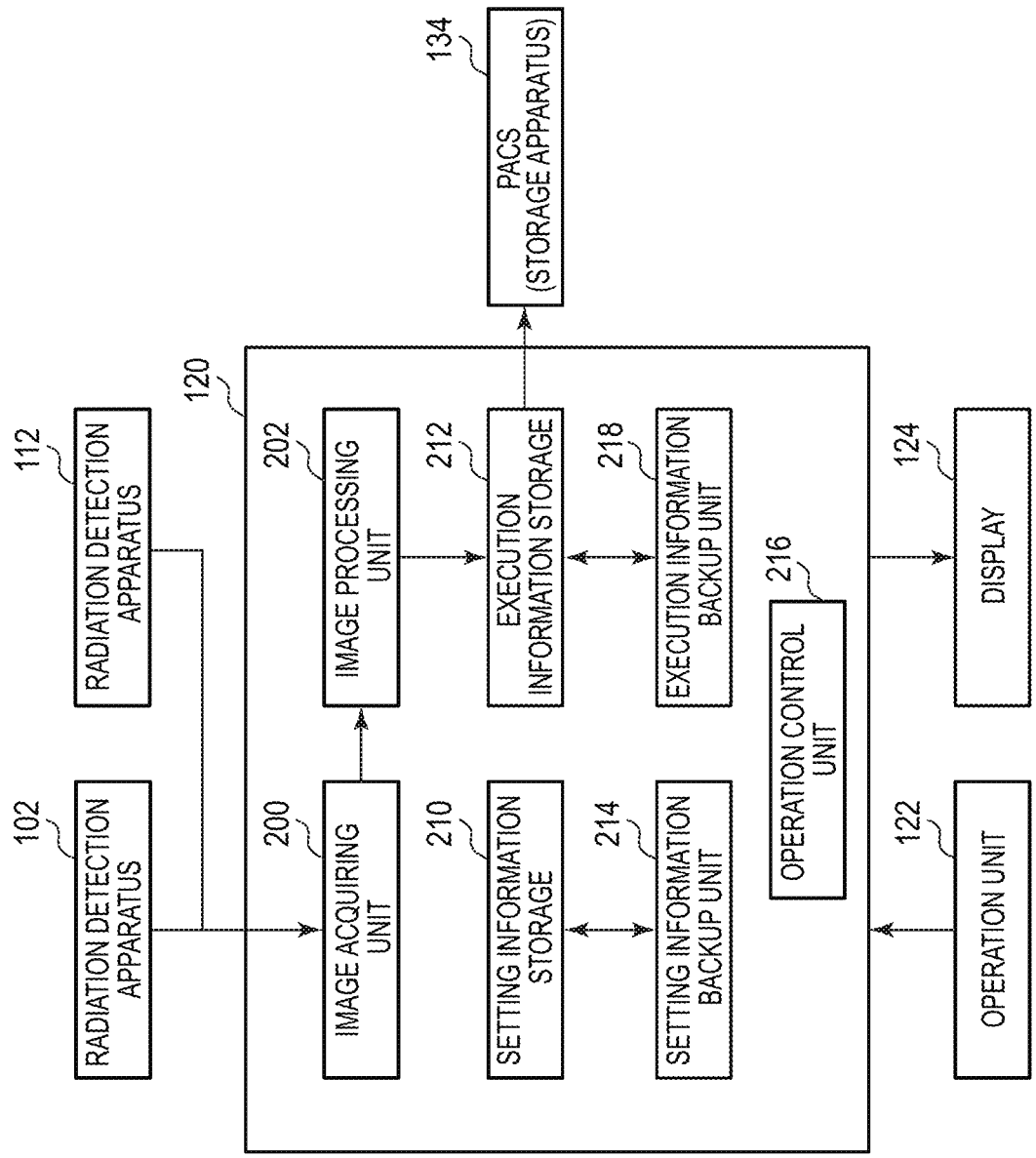

RADIATION IMAGING SYSTEM, CONTROL APPARATUS, CONTROL METHOD, AND COMPUTER READABLE MEDIUM

BACKGROUND

Field

The present disclosure relates to a radiation imaging system capable of performing radiation imaging, a control apparatus, a control method, and a computer readable medium, and more particularly, to a technology of restoring a failed component of the radiation imaging system.

Description of the Related Art

In recent years, radiation imaging systems has been installed in hospitals. When it is determined that a subject is required to be subjected to radiation imaging, an examination instruction is input to a terminal of a hospital information system (HIS), and an examination order is transmitted to a radiology department that is a recipient of an examination request. The radiation imaging system executes radiation imaging based on the examination order. A radiation image obtained from the radiation imaging is transferred to picture archiving and communication systems (PACS) or output to be printed.

When a component of the radiation imaging system fails, radiation imaging can no longer be performed. In view of this, it is proposed that, when an original apparatus has failed, the original apparatus is used without being completely stopped while a function thereof is limited, and a process that has been performed in the original apparatus is shared by another apparatus, to thereby execute an examination without interrupting a work flow (see, for example, Japanese Patent Application Laid-Open No. 2011-36560).

However, in the technology described in Japanese Patent Application Laid-Open No. 2011-36560, when the process is to be shared between the original apparatus and the other apparatus, the examination order is shared between the two apparatus, but setting information in the original apparatus is not shared by the other apparatus. When radiation imaging is performed through use of the other apparatus, an operator is required to make various settings in the other apparatus by referring to the setting information in the original apparatus. Accordingly, a period of time (downtime) during which radiation imaging cannot be performed is elongated.

SUMMARY

In view of the above, the present disclosure provides a radiation imaging system configured to reduce, even if a component of the radiation imaging system has failed, a period of time (downtime) during which radiation imaging cannot be performed.

According to at least one embodiment of the present disclosure, a radiation imaging system includes a setting information storage configured to store setting information to be used for radiation imaging, a setting information backup unit configured to back up the setting information stored in the setting information storage, and a control unit configured to restore, in a case the setting information storage has failed, the setting information in the setting information storage, based on the setting information backed up in the setting information backup unit.

Further features of the present disclosure will become apparent from the following description of exemplary embodiments with reference to the attached drawings.

BRIEF DESCRIPTION OF THE DRAWINGS

FIG. 8 is a diagram for illustrating the configuration of the control apparatus in the radiation imaging system according to at least one embodiment.

DESCRIPTION OF THE EMBODIMENTS

Exemplary embodiments of the present disclosure will now be described in detail in accordance with the accompanying drawings.

First Embodiment

Figure 1:
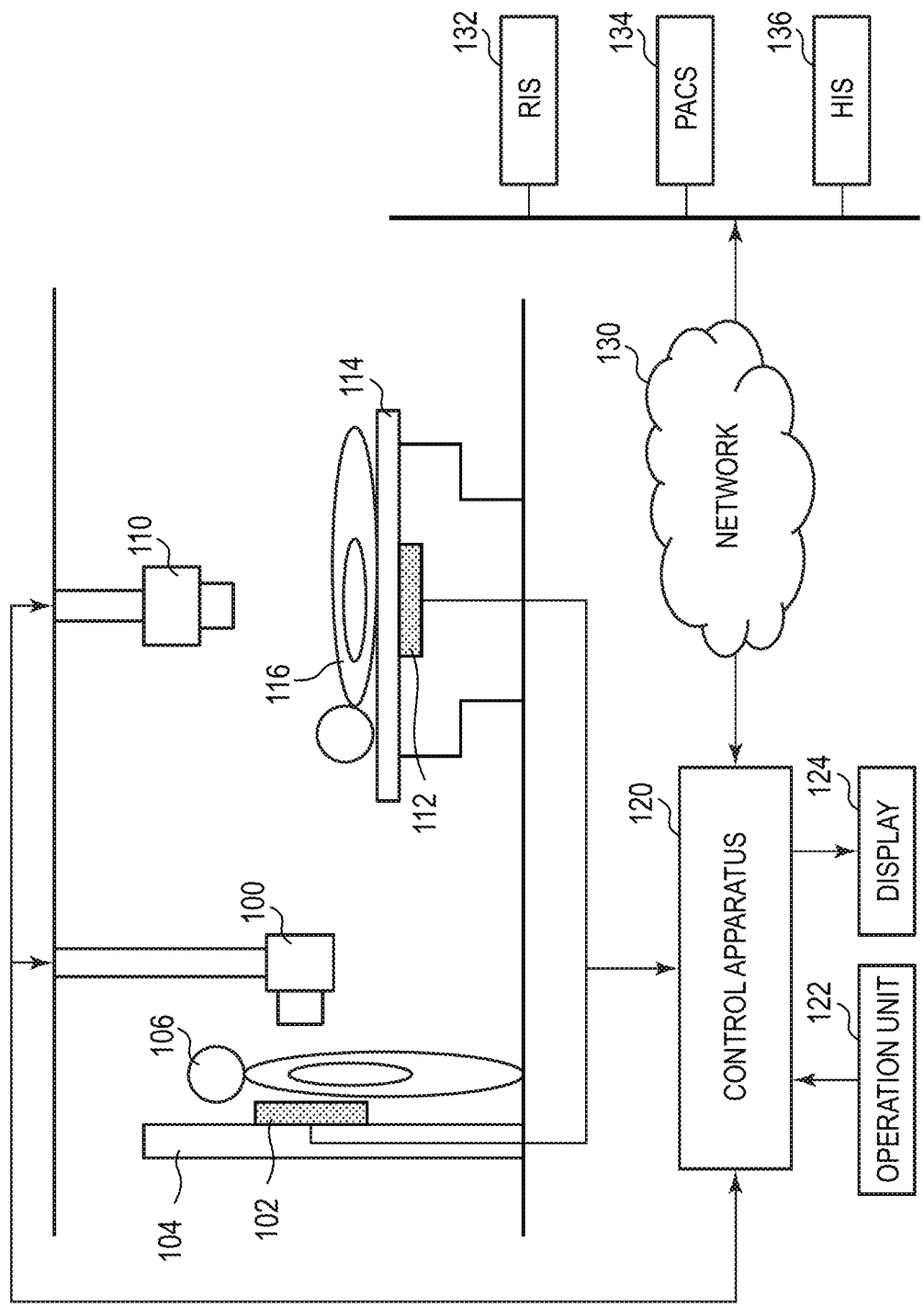
FIG. 1 is a diagram for illustrating an overall configuration of a radiation imaging system according to at least one embodiment.

Referring to FIG. 1 to FIG. 7, a first embodiment of the present disclosure is described. As illustrated in FIG. 1, two pairs of a radiation generator and a radiographic stand (table) are placed in a radiation imaging room. The radiation imaging room includes a radiation generator 100 configured to generate radiation, a radiation detection apparatus 102 configured to detect the radiation transmitted through a subject 106, and a radiographic stand 104 configured to support the radiation detection apparatus 102. The radiographic stand 104 is a standing-position radiographic stand. The radiation imaging room also includes a radiation generator 110 configured to generate radiation, a radiation detection apparatus 112 configured to detect the radiation transmitted through a subject 116, and a radiographic table 114 configured to support the radiation detection apparatus 112. The radiographic table 114 is a recumbent-position radiographic table.

The radiation imaging system includes a display 124 connected to a control apparatus 120 to display radiation images and various kinds of information, an operation unit 122 to be operated by an operator, and the control apparatus 120 configured to set radiation imaging conditions (e.g., tube voltage, tube current, and irradiation period) for each of the radiation generators 100 and 110, perform image processing on radiation images output from the radiation detection apparatus 102 and 112, and perform various kinds of control. The control apparatus 120 functions as a display control unit for the display 124.

The control apparatus 120 is connected to a radiology information system (RIS) 132 configured to transmit an examination order to the control apparatus 120 via a network 130, a PACS 134 configured to manage radiation images, and an HIS 136 configured to manage the progress of an examination.

When receiving the examination order via the RIS 132, a radiology department in, for example, a hospital adds, to the examination order, imaging information (e.g., radiation imaging conditions and an imaging procedure) related to radiation imaging, and transmits the examination order with the radiation imaging information to the control apparatus 120. The control apparatus 120 executes radiation imaging based on the received examination order. The control apparatus 120 then adds, to radiation images obtained from the radiation imaging, collateral information including the examination order, and outputs the radiation images with the collateral information.

The PACS 134 is a server mainly dedicated to image management. The PACS 134 includes a storage apparatus configured to store the radiation images and the collateral information. An operation of checking radiation images, detailed post-processing, a diagnostic operation, and the like are performed by using a high-definition monitor connected to the PACS 134. The radiation images output from the control apparatus 120 are transmitted to the PACS 134.

The HIS 136 is a hospital management system and includes a server configured to manage accounting information. When radiation imaging is to be performed, an operator inputs an examination instruction to a terminal of the HIS 136. Then, the examination instruction is transmitted from the HIS 136 to the radiology department in the hospital, which is a recipient of an examination request. The request information is referred to as an examination order. The examination order includes a name of a department sending an examination request, an examination item, private data of a subject, and the like. Examination execution information in the radiation imaging system is transmitted to the HIS 136. The execution information transmitted to the HIS 136 is used for examination progress management as well as for an accounting process after the examination.

The control apparatus 120, the MS 132, the PACS 134, and the HIS 136 are connected to one another via a network 130 formed of, for example, a local area network (LAN), a wide area network (WAN), or the like.

Each of these apparatuses includes at least one computer. The computer includes, for example, a main control unit such as a CPU and storage apparatuses such as a read only memory (ROM) and a random access memory (RAM). The computer can also include a communication unit such as a network card, an input/output unit such as a keyboard, a display, or a touch panel, and the like. Those components are connected to one another via a bus or the like, and are each controlled through execution of programs stored in the storage apparatus by the main control unit.

The control apparatus 120 is connected to the radiation generators 100 and 110. Specifically, the control apparatus 120 is connected to each of the radiation generators 100 and 110 via a wired or wireless network or a dedicated line. The control apparatus 120 sets radiation imaging conditions for radiation from each of the radiation generators 100 and 110 to control generation of the radiation from each of the radiation generators 100 and 110. Each of the radiation generators 100 and 110 functions as a radiation source configured to generate radiation. Each of the radiation generators 100 and 110 is implemented by, for example, an X-ray tube and emits radiation toward the subject 106 or 116 (for example, a specified region of the subject).

Each of the radiation generators 100 and 110 can apply the radiation to an intended irradiation range. Each of the radiation generators 100 and 110 is placed via a supporting unit located on a floor surface or a ceiling. In an irradiated surface of each of the radiation generators 100 and 110, a diaphragm (not shown) is configured to block the radiation. The operator controls the diaphragm configured to block the radiation to set the irradiation range of the radiation emitted from each of the radiation generators 100 and 110.

The radiation imaging system includes the radiation detection apparatus 102 and 112 configured to detect the radiation emitted from the radiation generators 100 and 110, respectively. The radiation detection apparatus 102 and 112 detect the radiation transmitted through the subjects 106 and 116, respectively, and output image data based on the radiation. The image data can also be referred to as radiation images.

Specifically, the radiation detection apparatus 102 and 112 respectively detect the radiation transmitted through the subjects 106 and 116 as charges corresponding to transmitted radiation doses. For example, each of the radiation detection apparatus 102 and 112 uses a direct conversion sensor configured to convert radiation directly to charges, for example, a-Se that converts radiation to charges, or an indirect sensor employing a scintillator, for example, CsI and a photoelectric conversion element, for example, a-Si. The radiation detection apparatus 102 and 112 also perform A/D conversion on the detected charges to generate the radiation images and output the generated radiation images to the control apparatus 120.

The operation unit 122 is configured to enable the radiation imaging system to be operated. For example, the operation unit 122 includes a mouse, an operation icon, or the like to receive input of various instructions from the operator to the individual components. For example, the display 124 is implemented by a liquid crystal display or the like to display various kinds of information to the operator (radiologist or doctor). The display 124 and the operation unit 122 can also be implemented as a touch panel in which the display 124 and the operation unit 122 are integrated.

The control apparatus 120 is connected to each of the radiation detection apparatus 102 and 112. Specifically, the control apparatus 120 is connected to each of the radiation detection apparatus 102 and 112 via a wired or wireless network or a dedicated line. The radiation detection apparatus 102 and 112 perform radiation imaging through use of the radiation emitted from the radiation generators 100 and 110, respectively, and output the radiation images to the control apparatus 120. The control apparatus 120 has a function of an application operating in the computer. The control apparatus 120 controls respective operations of the radiation detection apparatus 102 and 112 while outputting the radiation images to the display 124 or outputting a graphical user interface (GUI). The control apparatus 120 has a function of performing image processing such as noise removal, a gradation process, or an enhancement process for the radiation images output from the radiation detection apparatus 102 and 112. The control apparatus 120 can also perform image processing such as trimming or rotation for the radiation images output from the radiation detection apparatus 102 and 112. The display 124 displays the radiation images output from the control apparatus 120.

Figure 2:
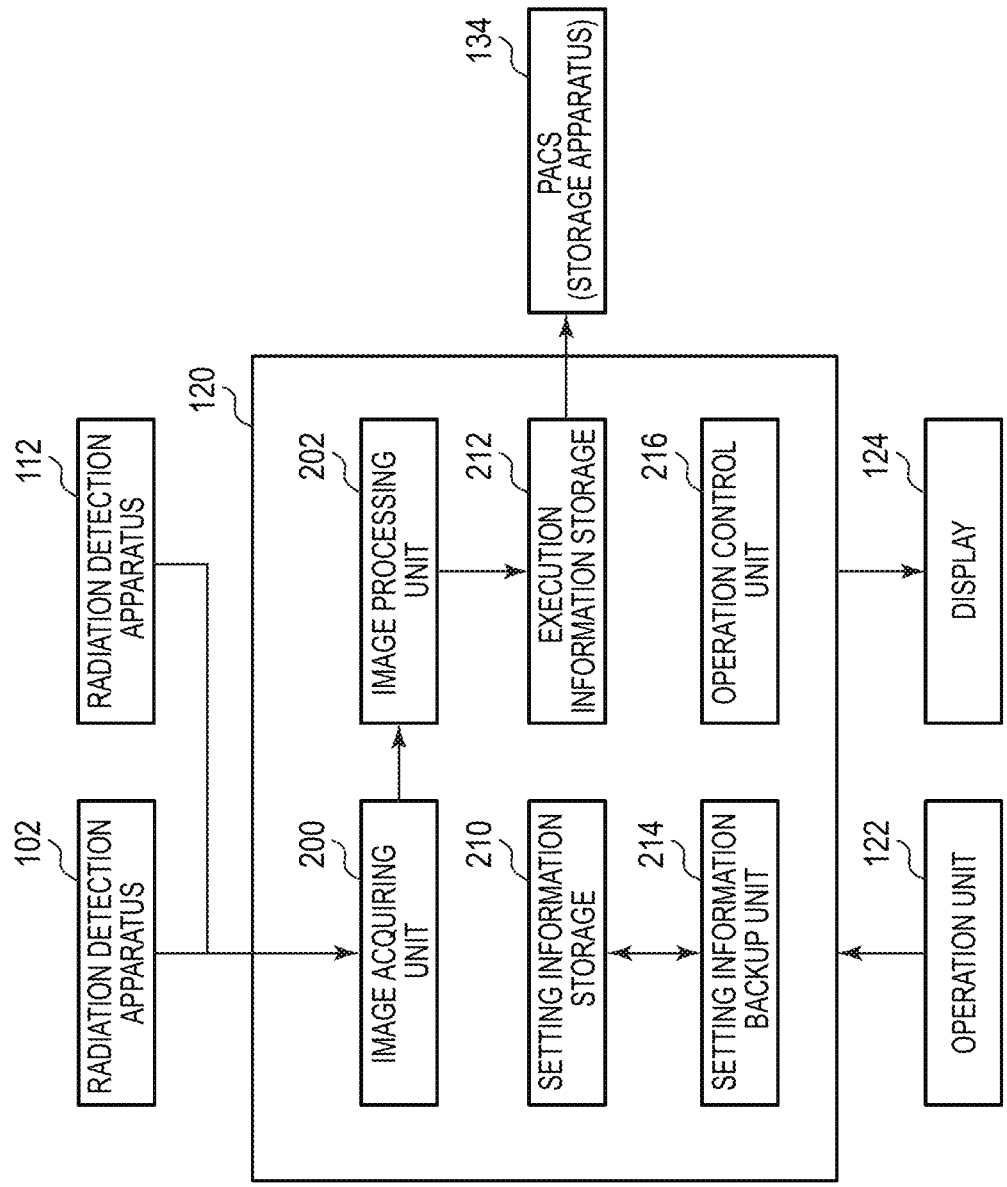
FIG. 2 is a diagram for illustrating a configuration of a control apparatus in the radiation imaging system according to at least one embodiment.

Referring to FIG. 2, details of the control apparatus 120 are described. As illustrated in FIG. 2, the control apparatus 120 includes an image acquiring unit 200 configured to acquire the radiation images (image data) output from the radiation detection apparatus 102 and 112 and an image processing unit 202 configured to perform image processing for the radiation images acquired by the image acquiring unit 200. The radiation images subjected to the image processing performed by the image processing unit 202 are output to the PACS (storage apparatus) 134.

The control apparatus 120 also includes a setting information storage 210 configured to store setting information related to radiation imaging settings, an execution information storage 212 configured to store execution information acquired through execution of radiation imaging, a setting information backup unit 214 configured to back up the setting information stored in the setting information storage 210 and store the backed-up setting information, and an operation control unit 216 configured to control the individual components of the control apparatus 120. The control apparatus 120 is configured such that the computer executes various kinds of processing based on the programs stored in the memories (ROM and RAM).

The setting information enables the radiation imaging system (control apparatus 120) to operate. The setting information is not output to the PACS (storage apparatus) 134, and remains in the control apparatus 120.

The setting information includes information related to each of the radiation detection apparatus 102 and 112 to be used for each imaging procedure (imaging protocol). For example, the setting information includes information (radiographic stand/table information) related to a radiographic stand and a radiographic table on which the radiation detection apparatus 102 and 112 are placed, information (type information) related to types of the radiation detection apparatus 102 and 112, information (installation position information) related to respective positions at which the radiation detection apparatus 102 and 112 are installed based on body positions of the subjects, and the like.

The setting information can also include calibration data for the radiation detection apparatus 102 and 112. The setting information storage 210 can also acquire, from white images obtained from radiation imaging performed using the radiation detection apparatus 102 and 112, the calibration data as correction data indicative of fluctuations in respective input/output characteristics of individual pixels in the radiation detection apparatus 102 and 112 by performing a process of, for example, determining reciprocal numbers, and store the calibration data.

The setting information can also include an image processing parameter set for each imaging procedure (imaging protocol). For example, the image processing parameter is set as the setting information for each of radiation imaging on anterior of a chest region, radiation imaging on a lateral side of the chest region, radiation imaging on anterior of an abdominal region, radiation imaging on a lateral side of the abdominal region, and the like.

The setting information backup unit 214 is normally in a state unconnected to the other components of the control apparatus 120 and unaffected by the other components. In such a state, the setting information backup unit 214 is in a state where a function thereof is limited and, for example, reading, writing, and updating cannot be performed. In other words, in the control apparatus 120, the setting information backup unit 214 is in a protected state. The setting information backup unit 214 is electrically connected to the setting information storage 210 as required. For example, the setting information backup unit 214 is electrically connected to the setting information storage 210 when backing up the setting information in the setting information storage 210. After backing up the setting information in the setting information storage 210, the setting information backup unit 214 is disconnected from the setting information storage 210.

The setting information backup unit 214 is also electrically connected to the setting information storage 210 when reading out the setting information stored in the setting information backup unit 214 and storing it in the setting information storage 210. After reading out the setting information stored in the setting information backup unit 214 and storing it in the setting information storage 210, the setting information backup unit 214 is disconnected from the setting information storage 210.

The setting information stored in the setting information storage 210 can have a file format different from that of the setting information stored in the setting information backup unit 214. For example, the setting information backup unit 214 can also compress the setting information to be backed up and store the compressed setting information.

The execution information includes the radiation imaging conditions, the radiation images, subject information, and the like. The execution information is output to the PACS (storage apparatus) 134. The control apparatus 120 causes the display 124 to display the radiation images output from the image processing unit 202. The display 124 displays the radiation images subjected to the image processing performed by the image processing unit 202 and output from the image processing unit 202. The operator can operate the image processing parameter in the image processing unit 202 via the operation unit 122.

The PACS (storage apparatus) 134 stores the radiation images output from the control apparatus 120. The PACS (storage apparatus) 134 stores the radiation images subjected to the image processing performed by the image processing unit 202. The PACS (storage apparatus) 134 can also store the radiation images in conjunction with the radiation imaging conditions, the subject information, and the like.

Figure 3:
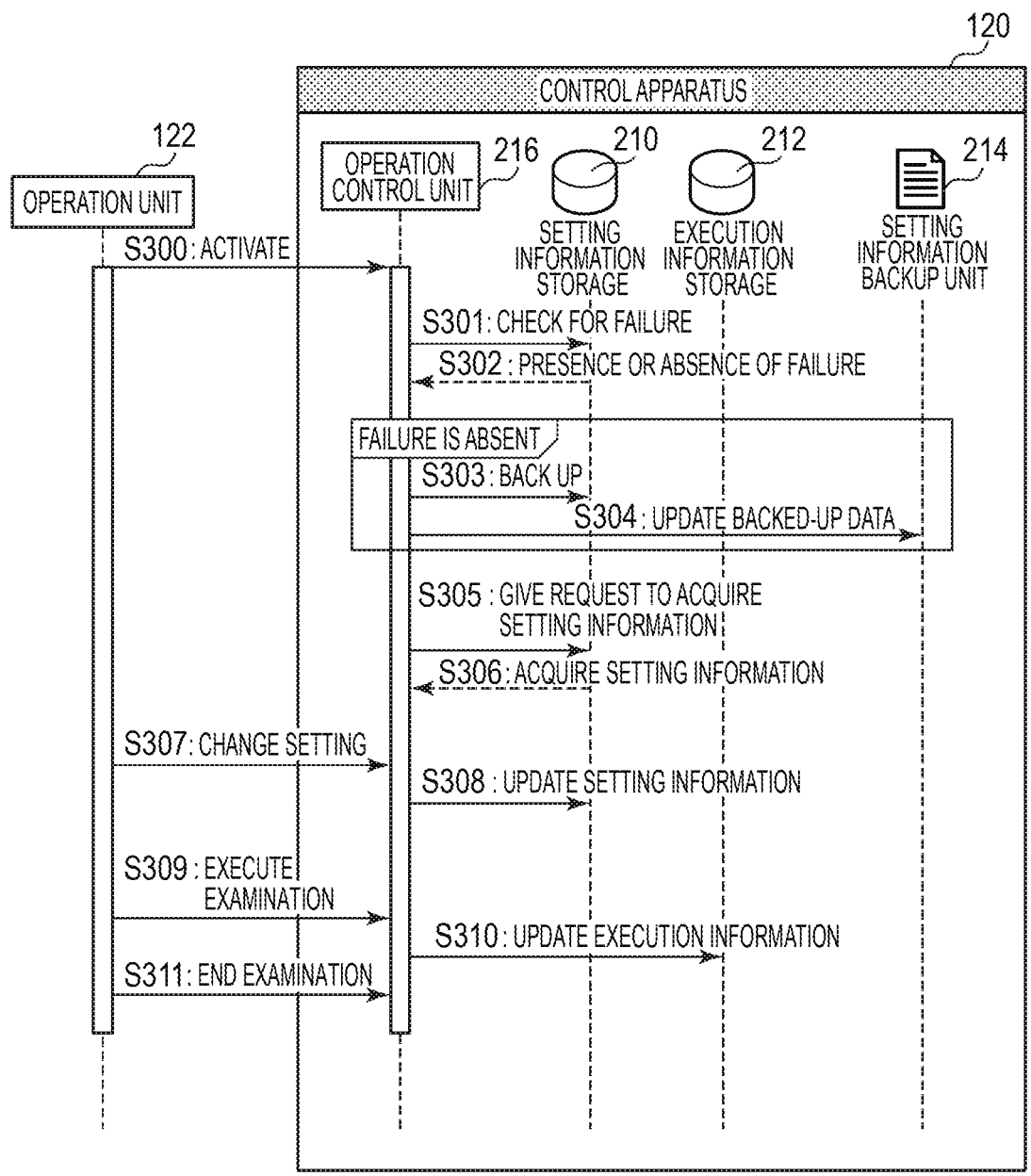
FIG. 3 is a diagram for illustrating an example of an operation of the control apparatus in the radiation imaging system according to at least one embodiment.

Next, referring to FIG. 3, a description is given of an operation of the control apparatus 120.

In Step S300, the operator activates the control apparatus 120 via the operation unit 122. Activation information in the operation unit 122 is transmitted to the operation control unit 216 of the control apparatus 120.

In Step S301, when the control apparatus 120 is activated, the operation control unit 216 determines, for the setting information storage 210, whether the setting information storage 210 has experienced a failure. Specifically, when the control apparatus 120 is activated, it is determined whether the setting information storage 210 has experienced a failure. A failure in the setting information storage 210 results from a physical failure caused by a hardware fault or from a software logical failure. The setting information storage 210 includes a storage medium that can experience the logical failure or the physical failure. The operation control unit 216 can also determine whether the logical failure or the physical failure has caused the failure in the setting information storage 210. When the setting information storage 210 experiences the logical failure, a logically faulty sector may have caused the failure. When the faulty sector is repaired, it may be possible to restore the setting information storage 210. When the setting information storage 210 is restored, it is also possible to change the determination by the operation control unit 216 such that there is no failure in the setting information storage 210.

In Step S302, when the setting information storage 210 does not experience a failure, the process advances to Step S303. When the setting information storage 210 experiences a failure, the process does not advance to Step S303, and an external apparatus (such as the display 124) is notified of the failure in the setting information storage 210.

In Step S303, when the setting information storage 210 did not experience a failure, the operation control unit 216 provides, to the setting information storage 210, an instruction to back up the setting information stored in the setting information storage 210. Thus, the operation control unit 216 determines whether the setting information storage 210 is to back up the setting information into the setting information backup unit 214 based on a failure situation resulting from the logical failure or the physical failure. The failure situation can also include information indicative of whether the setting information storage 210 experienced a failure, a factor of the failure, and information indicative of whether the setting information storage 210 can be self-restored.

In Step S304, the operation control unit 216 reads the setting information stored in the setting information storage 210 and backs up the setting information stored in the setting information storage 210 into the setting information backup unit 214. When backed-up data is already stored in the setting information backup unit 214, the backed-up data is updated (overwritten). Thus, in the current embodiment, when the control apparatus 120 is activated, the setting information stored in the setting information storage 210 is backed up.

Step S305 to Step S308 are steps of updating the setting information stored in the setting information storage 210. For example, the operator can change information related to each of the radiation detection apparatus 102 and 112 to be used for each imaging procedure (imaging protocol) or change the image processing parameter set for each imaging procedure (imaging protocol) via the operation unit 122. Accordingly, every time the operator changes the setting information, the changed setting information is stored in the setting information storage 210.

In Step S305, the operation control unit 216 requests the setting information storage 210 to acquire the setting information. Specifically, the operation control unit 216 requests the setting information storage 210 to acquire the currently stored setting information to be updated.

In Step S306, the operation control unit 216 acquires the setting information from the setting information storage 210. The operation control unit 216 acquires the information related to each of the radiation detection apparatus 102 and 112 to be used for each imaging procedure (imaging protocol) or acquires the image processing parameter set for each imaging procedure (imaging protocol) or the like.

In Step S307, the operator changes the setting information via the operation unit 122. For example, the operator changes the radiation detection apparatus 102 or 112 to be used for each imaging procedure (imaging protocol) or changes the image processing parameter set for each imaging procedure (imaging protocol).

In Step S308, the operation control unit 216 transmits the setting information changed in Step S307 to the setting information storage 210, where the setting information is updated. For example, when the radiation detection apparatus 102 or 112 to be used for each imaging procedure (imaging protocol) is changed, information related to the radiation imaging detection apparatus 102 or 112 after the change is stored as the setting information in the setting information storage 210. Alternatively, when the image processing parameter for each imaging procedure (imaging protocol) is changed, the image processing parameter after the change is stored as the setting information in the setting information storage 210.

Step S309 and Step S310 are steps of updating the execution information stored in the execution information storage 212. For example, the operator executes an examination via the operation unit 122 and performs radiation imaging through use of the radiation detection apparatus 102 or 112. The radiation imaging enables the execution information such as the radiation imaging conditions, the radiation image, and the subject information to be newly acquired. Accordingly, every time the operator executes radiation imaging, the execution information related to the radiation imaging is stored in the execution information storage 212.

In Step S309, the operator executes the examination via the operation unit 122. Specifically, the control apparatus 120 executes radiation imaging based on the examination order received via the operation unit 122. The radiation detection apparatus 102 or 112 detects the radiation transmitted through the subject 106 or 116 and outputs, to the control apparatus 120, the execution information including the radiation image corresponding to the radiation, the radiation imaging conditions, and the subject information.

In Step S310, the operation control unit 216 transmits the execution information acquired in Step S309 to the execution information storage 212, where the execution information is updated. The execution information stored in the execution information storage 212 can be output to the PACS (storage apparatus) 134.

In Step S311, after Step S310 is performed, the examination executed so far ends. After all the examinations end, the operator shuts down the control apparatus 120 via the operation unit 122.

In the present embodiment, when the control apparatus 120 (radiation imaging system) is activated, it is determined whether the setting information storage 210 experienced a failure. When the setting information storage 210 did not experience a failure, it is possible to back up the setting information into the setting information backup unit 214. Accordingly, even if the setting information in the setting information storage 210 is updated in the control apparatus 120, it is possible to back up the setting information.

Figure 4:
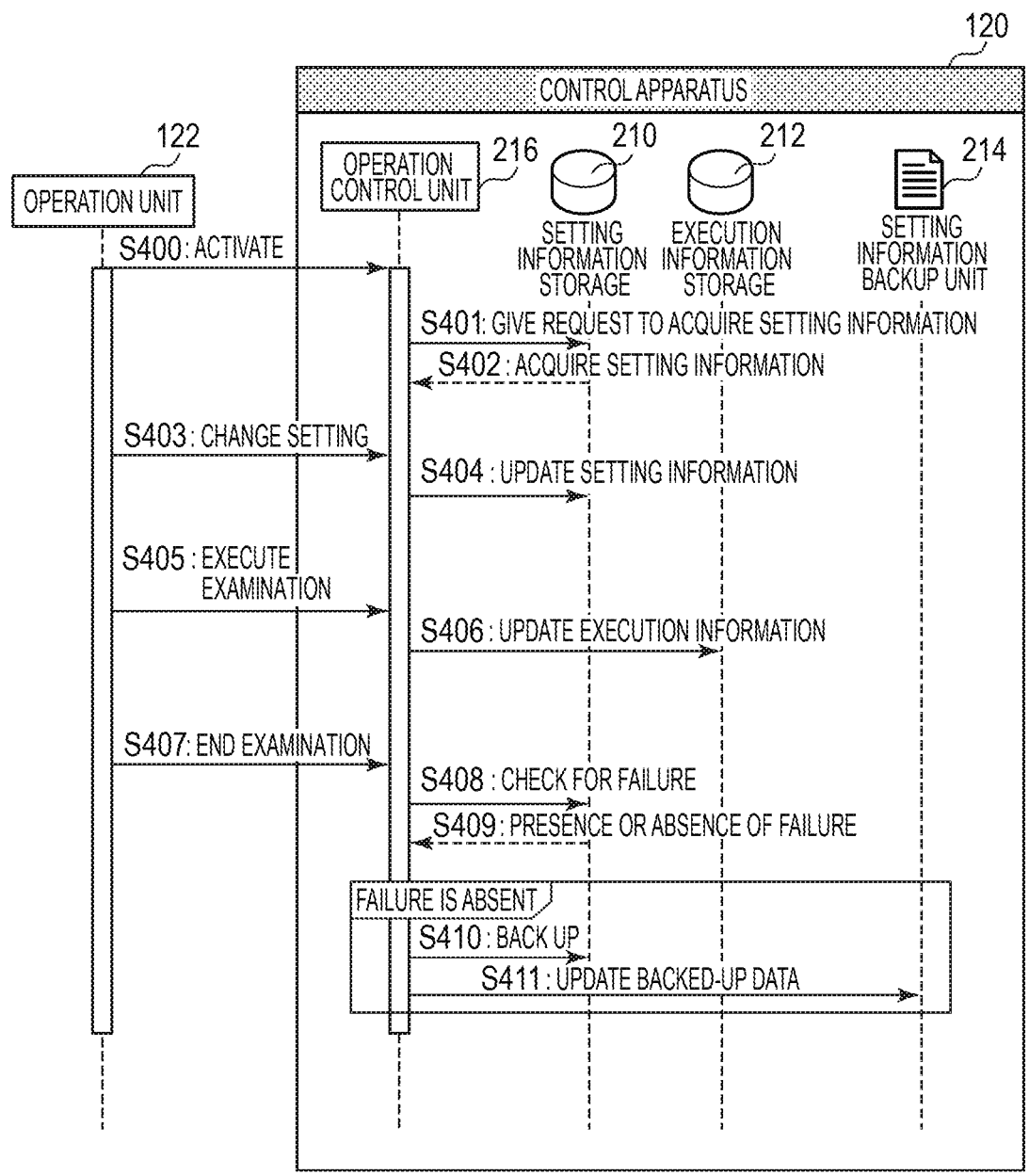
FIG. 4 is a diagram for illustrating an example of the operation of the control apparatus in the radiation imaging system according to at least one embodiment.

Next, referring to FIG. 4, a description is provided of an operation of the control apparatus 120. The operation in FIG. 4 is different from the operation in FIG. 3 in that, when the control apparatus 120 is shut down, the setting information is backed up.

In Step S400, the operator activates the control apparatus 120 via the operation unit 122. Activation information in the operation unit 122 is transmitted to the operation control unit 216 of the control apparatus 120.

In Step S401, the operation control unit 216 requests the setting information storage 210 to acquire the setting information. Specifically, the operation control unit 216 requests the setting information storage 210 to acquire the currently stored setting information to be updated.

In Step S402, the operation control unit 216 acquires the setting information from the setting information storage 210.

In Step S403, the operator changes the setting information via the operation unit 122.

In Step S404, the operation control unit 216 transmits the setting information changed in Step S403 to the setting information storage 210, where the setting information is updated.

In Step S405, the operator executes the examination via the operation unit 122. Specifically, the control apparatus 120 executes radiation imaging based on the examination order received via the operation unit 122.

In Step S406, the operation control unit 216 transmits the execution information acquired in Step S405 to the execution information storage 212, where the execution information is updated.

In Step S407, after the processing of Step S406 is performed, the examination executed so far ends. After all the examinations end, the operator shuts down the control apparatus 120 via the operation unit 122.

In Step S408, when an operation of shutting down the control apparatus 120 is started, before a function of the control apparatus 120 is stopped, the operation control unit 216 determines if, for the setting information storage 210, whether the setting information storage 210 experienced a failure. The operation control unit 216 determines whether the setting information storage 210 experienced a failure resulting from a logical failure or a physical failure.

In Step S409, when the setting information storage 210 did not experience a failure, the process advances to Step S410. When the setting information storage 210 experienced a failure, the process does not advance to Step S410, and an external apparatus (such as the display 124) is notified of the failure in the setting information storage 210.

In Step 410, when the setting information storage 210 does not experience a failure, the operation control unit 216 provides, to the setting information storage 210, an instruction to back up the setting information stored in the setting information storage 210. Thus, the operation control unit 216 determines whether the setting information storage 210 experienced a failure resulting from a logical failure or a physical failure, and then determines whether the setting information is to be backed up.

In Step S411, the operation control unit 216 reads the setting information stored in the setting information storage 210 and backs up the setting information stored in the setting information storage 210 into the setting information backup unit 214. When backed-up data is already stored in the setting information backup unit 214, the backed-up data is updated (overwritten). Thus, in the present embodiment, when the control apparatus 120 is shut down, the setting information stored in the setting information storage 210 is backed up.

In the present embodiment, when the control apparatus 120 is shut down, the control apparatus 120 determines whether the setting information storage 210 experienced a failure. When the setting information storage 210 did not experience a failure, it is possible to back up the setting information into the setting information backup unit 214. Accordingly, even if the setting information in the setting information storage 210 is updated in the control apparatus 120, it is possible to appropriately back up the setting information.

Figure 5:
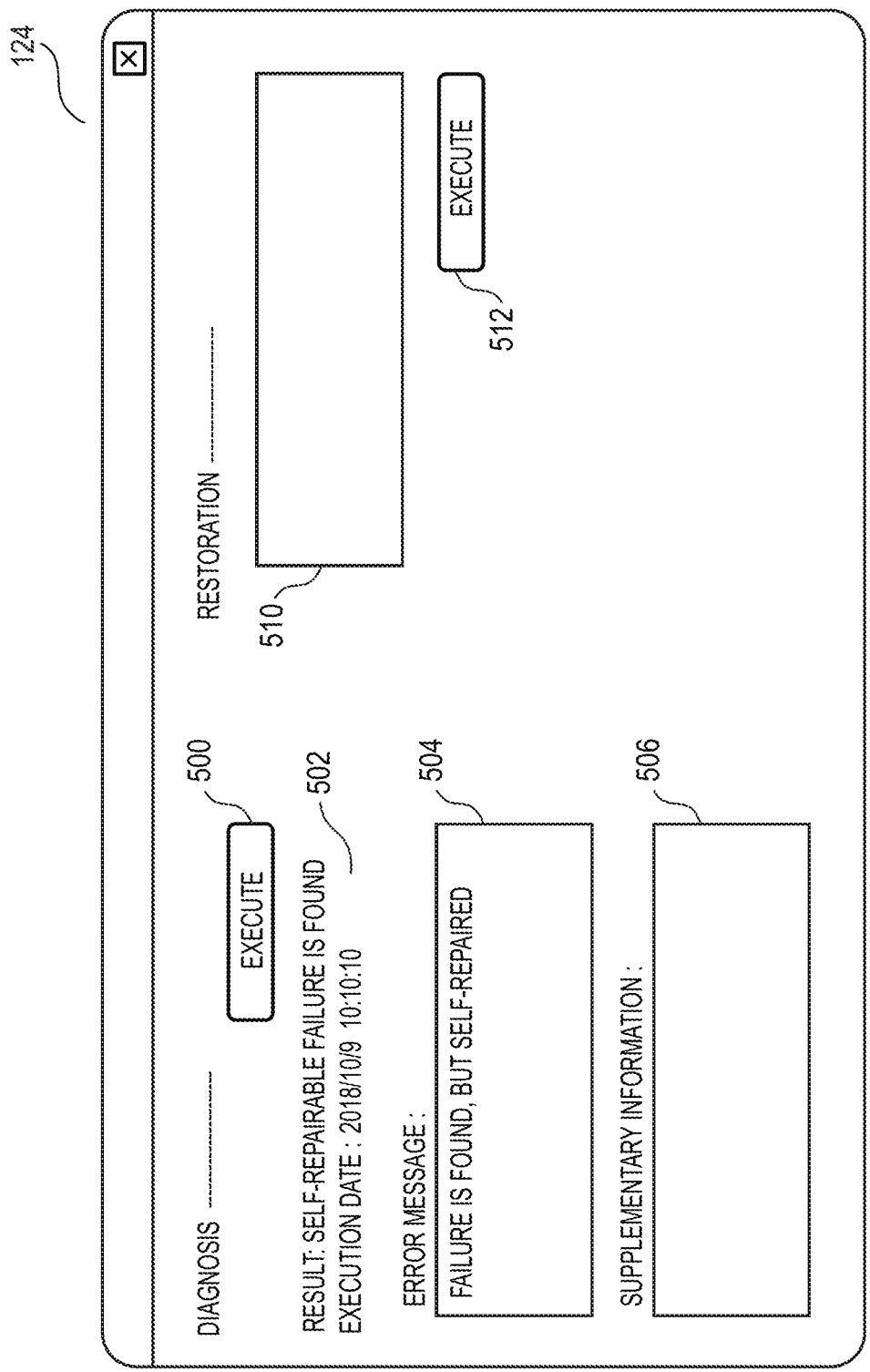
FIG. 5 is a diagram for illustrating an example of a display screen on a display in the radiation imaging system according to at least one embodiment.
Figure 6:
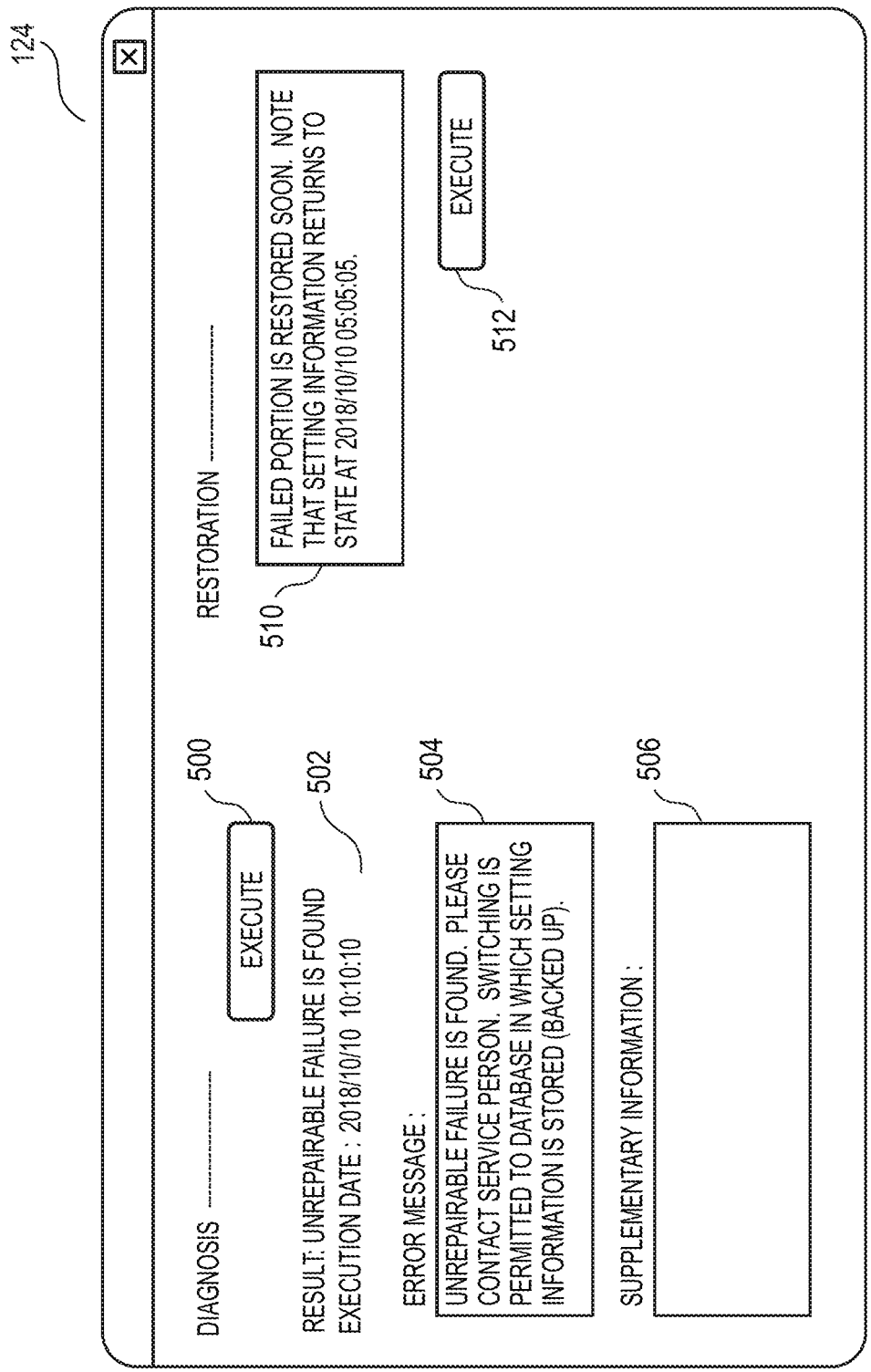
FIG. 6 is a diagram for illustrating an example of the display screen on the display in the radiation imaging system of according to at least one embodiment.

Next, referring to FIG. 5 and FIG. 6, a description is provided of diagnosis and restoration of the setting information storage 210. FIG. 5 is a diagram illustrating an example of display on the display 124 at a time when the setting information storage 210 experiences a self-repairable failure. The diagnosis of the setting information storage 210 is illustrated on a left side of FIG. 5, while the restoration thereof is illustrated on a right side of FIG. 5.

The display 124 displays an execution icon 500 for executing the diagnosis of the setting information storage 210, a result and an execution date 502 of the diagnosis of the setting information storage 210, an error message 504 indicating caution when the setting information storage 210 experiences a failure, and supplementary information 506 related to the diagnosis of the setting information storage 210.

When the diagnosis of the setting information storage 210 is performed, the operator presses the execution icon 500. When the execution icon 500 is pressed, the operation control unit 216 executes the diagnosis of the setting information storage 210. In the diagnosis of the setting information storage 210, a physical failure caused by a hardware fault and a software logical failure are diagnosed.

When the setting information storage 210 experiences the logical failure, it is possible to restore the setting information storage 210 by repairing a faulty sector. It is assumed herein that, as displayed in the diagnosis result/execution date 502, as a result of the diagnosis, a self-repairable failure is found. In the example illustrated in FIG. 5, the execution date is 2018/10/9 10:10:10 and "FAILURE IS FOUND, BUT SELF-REPAIRED" is displayed as the error message 504.

When it is diagnosed that the setting information storage 210 can be self-restored, the setting information storage 210 is self-restored. When the setting information storage 210 can be self-restored, the setting information backup unit 214 is not required to read out the stored setting information and store it in the setting information storage 210. When the setting information storage 210 is self-restored, the radiation imaging system can execute a normal operation (such as radiation imaging). When the setting information storage 210 can be self-restored, it is also possible to back up the setting information stored in the setting information storage 210. Specifically, when the setting information storage 210 can be self-restored, the setting information stored in the setting information storage 210 is read out. Then, the setting information backup unit 214 backs up the setting information stored in the setting information storage 210.

FIG. 6 is a diagram illustrating an example of display on the display 124 at a time when the setting information storage 210 experiences a self-unrepairable failure. The diagnosis of the setting information storage 210 is illustrated on a left side of FIG. 6, while the restoration thereof is illustrated on a right side of FIG. 6.

When the diagnosis of the setting information storage 210 is performed, the operator presses the execution icon 500. When the execution icon 500 is pressed, the operation control unit 216 executes the diagnosis of the setting information storage 210. In the diagnosis of the setting information storage 210, a physical failure caused by a hardware fault and a software logical failure are diagnosed.

It is assumed herein that, as displayed in the diagnosis result/execution date 502, as a result of the diagnosis, an unrepairable failure is found. In the example illustrated in FIG. 6, the execution date is 2018/10/10 10:10:10. As the error message 504, "UNREPAIRABLE FAILURE IS FOUND. PLEASE CONTACT SERVICE PERSON. SWITCHING IS PERMITTED TO DATABASE IN WHICH SETTING INFORMATION IS STORED (BACKED-UP)" is displayed. This enables the operator to recognize that the setting information storage 210 cannot be self-restored and contacting a service person to restore the setting information storage 210 is required.

On the display 124, a restoration message 510 related to restoration and an execution icon 512 for executing restoration are displayed.

When the setting information storage 210 experiences a self-unrepairable failure, the execution icon 512 for executing restoration becomes valid. When the operator presses the execution icon 512, the setting information backup unit 214 reads out the stored setting information stored and stores it in the setting information storage 210. The setting information backup unit 214 then restores the setting information in the setting information storage 210.

In an example illustrated in FIG. 6, as the restoration message 510, "FAILED PORTION IS RESTORED SOON. NOTE THAT SETTING INFORMATION RETURNS TO STATE AT 2018/10/10 05:05:05" is displayed. This enables the operator to recognize that, when the setting information storage 210 is restored, the setting information dates back to the previously backed-up setting information, and the current setting information is switched to the previous setting information.

Figure 7:
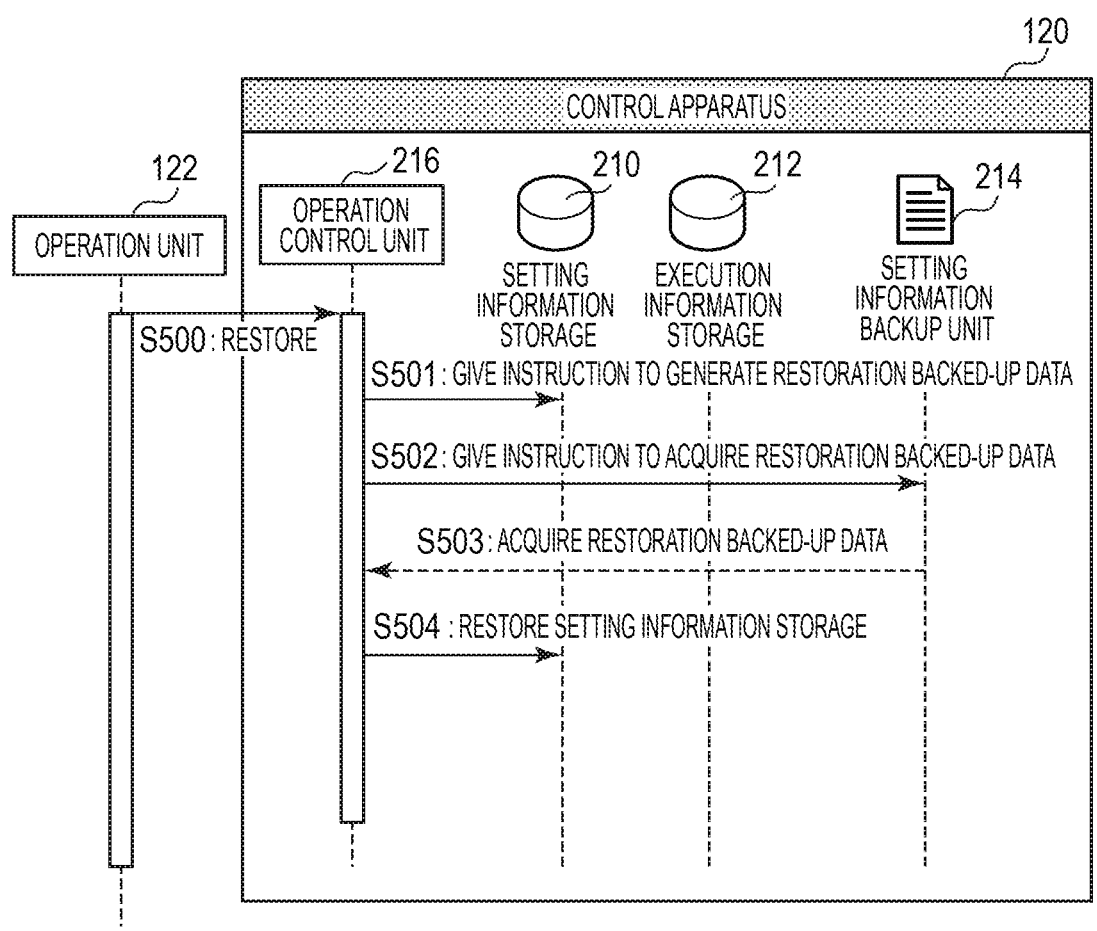
FIG. 7 is a diagram for illustrating an example of the operation of the control apparatus in the radiation imaging system according to at least one embodiment.

A description is now provided of an operation of restoring the setting information storage 210 with respect to FIG. 7.

In Step S500, the operator presses the execution icon 512 for executing restoration, which is displayed on the display 124. The restoration information is transmitted to the operation control unit 216 in the control apparatus 120. At this time, the control apparatus 120 is activated by another radiation imaging system (another control apparatus) or activated in a safe mode. In the safe mode, the control apparatus 120 can be activated to operate in a minimum required system environment. In the safe mode, the operation of restoring the setting information storage 210 can be executed.

In Step S501, the operation control unit 216 provides, to the setting information storage 210, an instruction to generate restoration backed-up data related to the setting information. The operation control unit 216 determines whether there has been a change in the setting information stored in the setting information storage 210 since the setting information was backed up. For example, in a mode illustrated in FIG. 3, when the control apparatus 120 is activated, it is determined whether the setting information stored in the setting information storage 210 experienced a failure, and the setting information is backed up into the setting information backup unit 214. The setting information changed in Step S307 has not been backed up in the setting information backup unit 214. When the setting information, which has not been backed up in the setting information backup unit 214 is valid (the setting information has no failure), it is possible to transmit the setting information, which has not been backed up in the setting information backup unit 214, to the setting information backup unit 214.

In Step S502, the operation control unit 216 provides an instruction to acquire the restoration backed-up data related to the setting information from the setting information backup unit 214. In other words, the operation control unit 216 provides an instruction to acquire the setting information stored in the setting information backup unit 214.

In Step S503, the operation control unit 216 acquires the restoration backed-up data related to the setting information from the setting information backup unit 214. In other words, the operation control unit 216 acquires the setting information stored in the setting information backup unit 214.

In Step S504, the operation control unit 216 restores the setting information storage 210 using the setting information stored in the setting information backup unit 214. Specifically, the setting information stored in the setting information storage 210 is replaced with the setting information stored in the setting information backup unit 214 to be updated.

As described above, the radiation imaging system according to the present embodiment includes the image acquiring unit 200 configured to acquire a radiation image based on radiation, the setting information storage 210 configured to store setting information to be used for radiation imaging, the setting information backup unit 214 configured to back up the setting information stored in the setting information storage 210, and the operation control unit 216 configured to restore, when the setting information storage 210 has failed, the setting information in the setting information storage 210 based on the setting information backed up in the setting information backup unit 214.

Accordingly, even if the setting information storage 210, which is a component of the control apparatus 120 has failed, it is possible to restore the setting information in the setting information storage 210 based on the setting information backed up in the setting information backup unit 214. This can reduce a period of time (downtime) during which radiation imaging cannot be performed. In the above-described example, the setting information storage 210 experienced a failure. However, the present embodiment is applicable in the event that any other component of the control apparatus 120 experiences a failure.

Second Embodiment

Referring to FIG. 8, a second embodiment of the present disclosure will be described. The second embodiment is different from the first embodiment in that an execution information backup unit 218 configured to back up the execution information stored in the execution information storage 212 is included.

The execution information backup unit 218 is typically unconnected to the other components of the control apparatus 120 and unaffected by the other components. In such a state, the execution information backup unit 218 is in a state where a function thereof is limited and, for example, reading, writing, and updating cannot be performed. In other words, in the control apparatus 120, the execution information backup unit 218 is in a protected state. The execution information backup unit 218 is electrically connected to the execution information storage 212 as required. For example, the execution information backup unit 218 is electrically connected to the execution information storage 212 when backing up the execution information in the execution information storage 212. After backing up the execution information in the execution information storage 212, the execution information backup unit 218 is disconnected from the execution information storage 212.

The execution information backup unit 218 is also electrically connected to the execution information storage 212 when reading out the execution information stored in the execution information backup unit 218 and storing it in the execution information storage 212. After reading out the execution information stored in the execution information backup unit 218 and storing it in the execution information storage 212, the execution information backup unit 218 is disconnected from the execution information storage 212.

A backup capacity for the execution information in the execution information storage 212 is greater than a backup capacity for the setting information in the setting information storage 210. Accordingly, when the execution information stored in the execution information storage 212 is output to the PACS (storage apparatus) 134, the operation control unit 216 can also delete the backed-up data of the execution information in the execution information backup unit 218. At this time, the operation control unit 216 can also initialize the execution information storage 212. This is because, when the execution information is output to the PACS (storage apparatus) 134, the execution information is protected by the PACS (storage apparatus) 134. The operator can observe the radiation images and the like using the execution information output to the PACS (storage apparatus) 134.

As illustrated in FIGS. 5 and 6, it is also possible to simultaneously diagnose the setting information storage 210 and the execution information storage 212. The operator presses the execution icon 500. When the execution icon 500 is pressed, the operation control unit 216 executes the diagnosis of the setting information storage 210 and the execution information storage 212. In the diagnosis of the setting information storage 210 and the execution information storage 212, a physical failure caused by a hardware fault and a software logical failure are diagnosed.

The operation control unit 216 can determine which of the setting information storage 210 or the execution information storage 212 has experienced a failure. When the setting information storage 210 experiences a failure, the control apparatus 120 causes the display 124 to display that the setting information storage 210 experienced a failure. When the execution information storage 212 experiences a failure, the control apparatus 120 causes the display 124 to display that the execution information storage 212 experienced a failure. When the setting information storage 210 or the execution information storage 212 experience a failure, the operation control unit 216 determines what kind of failure the setting information storage 210 or the execution information storage 212 experienced.

When it is diagnosed that the setting information storage 210 or the execution information storage 212 can be self-restored, the setting information storage 210 or the execution information storage 212 is self-restored.

When it is diagnosed that the setting information storage 210 or the execution information storage 212 cannot be self-restored, the operation control unit 216 uses the setting information stored in the setting information backup unit 214 to restore the setting information storage 210 or uses the execution information stored in the execution information backup unit 218 to restore the execution information storage 212.

Accordingly, even if the execution information storage 212, which is a component of the control apparatus 120, has failed, it is possible to restore the execution information in the execution information storage 212 based on the execution information backed up in the execution information backup unit 218.

According to the first and second embodiments, even when a component of the radiation imaging system has failed, a period of time (downtime) during which radiation imaging cannot be performed can be reduced.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-224270, filed Nov. 29, 2018, which is hereby incorporated by reference herein in its entirety.

What is claimed is:

1. A radiation imaging system comprising:
   a setting information storage configured to store setting information to be used for radiation imaging;
   a setting information backup unit configured to back up the setting information stored in the setting information storage; and
   a control unit configured to restore, in a case the setting information storage experiences a self-unrepairable failure, the setting information in the setting information storage based on the setting information backed up in the setting information backup unit,
   wherein the control unit causes the setting information backup unit to read out the setting information stored in the setting information backup unit and store the setting information in the setting information storage and restore the setting information in the setting information storage.

2. The radiation imaging system according to claim 1, wherein the setting information includes information related to a radiation detection apparatus to be used for each imaging procedure.

3. The radiation imaging system according to claim 1, wherein the setting information includes an image processing parameter set for each imaging procedure.

4. A radiation imaging system comprising:
   a setting information storage configured to store setting information to be used for radiation imaging;
   a setting information backup unit configured to back up the setting information stored in the setting information storage; and
   a control unit configured to restore, in a case the setting information storage has failed, the setting information in the setting information storage, based on the setting information backed up in the setting information backup unit;
   wherein the setting information backup unit is connected to the setting information storage when backing up the setting information in the setting information storage, and the setting information backup unit is disconnected from the setting information storage after backing up the setting information in the setting information storage.

5. The radiation imaging system according to claim 4, wherein the control unit is configured to determine, based on a failure situation in the setting information storage, whether the setting information stored in the setting information storage is to be backed up into the setting information backup unit.

6. The radiation imaging system according to claim 5, wherein, when the setting information storage does not experience a failure, the setting information backup unit backs up the setting information.

7. The radiation imaging system according to claim 4, wherein in a case where the radiation imaging system is activated or a case where the radiation imaging system is shut down, the control unit determines whether the setting information storage experienced a failure.

8. The radiation imaging system according to claim 4, wherein, in a case the setting information storage experiences a self-repairable failure, the control unit causes the setting information storage to be self-restored.

9. The radiation imaging system according to claim 4, further comprising:
an execution information storage configured to store execution information acquired through execution of radiation imaging; and
an execution information backup unit configured to back up the execution information stored in the execution information storage.

10. The radiation imaging system according to claim 9, wherein the control unit is configured to determine whether the setting information storage or the execution information storage experienced a failure.

11. A radiation imaging system comprising:
a setting information storage configured to store setting information to be used for radiation imaging;
a setting information backup unit configured to back up the setting information stored in the setting information storage; and
a control unit configured to restore, in a case the setting information storage has failed, the setting information in the setting information storage, based on the setting information backed up in the setting information backup unit,
wherein the setting information backup unit is connected to the setting information storage when reading out the setting information stored in the setting information backup unit and storing the setting information in the setting information storage, and the setting information backup unit is disconnected from the setting information storage after reading out the setting information stored in the setting information backup unit and storing the setting information in the setting information storage.

12. The radiation imaging system according to claim 11, wherein the setting information includes information related to a radiation detection apparatus to be used for each imaging procedure.

13. The radiation imaging system according to claim 11, wherein the setting information includes an image processing parameter set for each imaging procedure.

14. A control apparatus comprising:
a setting information storage configured to store setting information to be used for radiation imaging;
a setting information backup unit configured to back up the setting information stored in the setting information storage; and
a control unit configured to restore, in a case the setting information storage experiences a self-unrepairable failure, the setting information in the setting information storage; based on the setting information backed up in the setting information backup unit,
wherein the control unit causes the setting information backup unit to read out the setting information stored in the setting information backup unit and store the setting information in the setting information storage and restore the setting information in the setting information storage.

15. A control method comprising:
storing setting information to be used for radiation imaging in a setting information storage;
backing up the stored setting information into a setting information backup unit; and
restoring, in a case the setting information storage experiences a self-unrepairable failure, the setting information in the setting information storage based on the setting information backed up in the setting information backup unit,
wherein the restoring the setting information including:
reading out the setting information stored in the setting information backup unit;
storing the setting information in the setting information storage; and
restoring the setting information in the setting information storage.

16. The control method according to claim 15, wherein the setting information includes information related to a radiation detection apparatus to be used for each imaging procedure.

17. The control method according to claim 15, wherein the setting information includes an image processing parameter set for each imaging procedure.

18. A control method comprising:
storing setting information to be used for radiation imaging in a setting information storage;
backing up the stored setting information into a setting information backup unit; and
restoring, in a case the setting information storage has failed, the setting information in the setting information storage, based on the setting information backed up in the setting information backup unit,
wherein the setting information backup unit is connected to the setting information storage when backing up the setting information in the setting information storage, and the setting information backup unit is disconnected from the setting information storage after backing up the setting information in the setting information storage.

19. The control method according to claim 18, further comprising determining, based on a failure situation in the setting information storage, whether the setting information stored in the setting information storage is to be backed up into the setting information backup unit.

20. The control method according to claim 19, wherein, when the setting information storage does not experience a failure, the setting information is backed up.

21. The control method according to claim 18, further comprising, in a case where a radiation imaging system is activated or a case where the radiation imaging system is shut down, determining whether the setting information storage experienced a failure.

22. The control method according to claim 18, further comprising, in a case the setting information storage experiences a self-repairable failure, causing the setting information storage to be self-restored.

23. The control method according to claim 18, further comprising:

storing execution information acquired through execution of radiation imaging in an execution information storage; and backing up the stored execution information into an execution information backup unit.

24. The control method according to claim 23, further comprising determining whether the setting information storage or the execution information storage experienced a failure.

25. A control method comprising:

storing setting information to be used for radiation imaging in a setting information storage;

backing up the stored setting information into a setting information backup unit; and restoring, in a case the setting information storage has failed, the setting information in the setting information storage, based on the setting information backed up in the setting information backup unit, wherein the setting information backup unit is connected to the setting information storage when reading out the setting information stored in the setting information backup unit and storing the setting information in the setting information storage, and the setting information backup unit is disconnected from the setting information storage after reading out the setting information stored in the setting information backup unit and storing the setting information in the setting information storage.

26. The control method according to claim 25, wherein the setting information includes information related to a radiation detection apparatus to be used for each imaging procedure.

27. The control method according to claim 25, wherein the setting information includes an image processing parameter set for each imaging procedure.

28. A non-transitory computer readable medium storing a program for causing a computer to execute a control method, the control method comprising:

storing setting information to be used for radiation imaging in a setting information storage;

backing up the stored setting information into a setting information backup unit; and restoring, in a case the setting information storage experiences a self-unrepairable failure, the setting information in the setting information storage, based on the setting information backed up in the setting information backup unit, wherein the restoring the setting information including:

reading out the setting information stored in the setting information backup unit;

storing the setting information in the setting information storage; and restoring the setting information in the setting information storage.

29. A control apparatus comprising:

a setting information storage configured to store setting information to be used for radiation imaging;

a setting information backup unit configured to back up the setting information stored in the setting information storage; and a control unit configured to restore, in a case the setting information storage has failed, the setting information in the setting information storage, based on the setting information backed up in the setting information backup unit, wherein the setting information backup unit is connected to the setting information storage when backing up the setting information in the setting information storage, and the setting information backup unit is disconnected from the setting information storage after backing up the setting information in the setting information storage.

30. A control apparatus comprising:

a setting information storage configured to store setting information to be used for radiation imaging;

a setting information backup unit configured to back up the setting information stored in the setting information storage; and a control unit configured to restore, in a case the setting information storage has failed, the setting information in the setting information storage, based on the setting information backed up in the setting information backup unit, wherein the setting information backup unit is connected to the setting information storage when reading out the setting information stored in the setting information backup unit and storing the setting information in the setting information storage, and the setting information backup unit is disconnected from the setting information storage after reading out the setting information stored in the setting information backup unit and storing the setting information in the setting information storage.

* * * * *